(12) United States Patent
Kuroda et al.

(10) Patent No.: US 9,944,976 B2
(45) Date of Patent: Apr. 17, 2018

(54) METHOD FOR STIRRING SOLUTION

(71) Applicant: Toray Industries, Inc., Tokyo (JP)

(72) Inventors: Toshihiko Kuroda, Kamakura (JP);
Hitoshi Nobumasa, Kamakura (JP)

(73) Assignee: Toray Industries, Inc. (JP)

( * ) Notice: Subject to any disclaimer, the term of this patent is extended or adjusted under 35 U.S.C. 154(b) by 833 days.

(21) Appl. No.: 14/381,715

(22) PCT Filed: Feb. 27, 2013

(86) PCT No.: PCT/JP2013/055117
§ 371 (c)(1),
(2) Date: Aug. 28, 2014

(87) PCT Pub. No.: WO2013/129469
PCT Pub. Date: Sep. 6, 2013

(65) Prior Publication Data
US 2015/0045250 A1  Feb. 12, 2015

(30) Foreign Application Priority Data
Feb. 29, 2012  (JP) ................................. 2012-043704

(51) Int. Cl.
*G01N 33/53* (2006.01)
*C12Q 1/68* (2006.01)
*G01N 33/543* (2006.01)
*B01F 9/00* (2006.01)
*G01N 3/16* (2006.01)
*G01N 35/00* (2006.01)

(52) U.S. Cl.
CPC .......... *C12Q 1/6837* (2013.01); *B01F 9/0003* (2013.01); *G01N 33/5306* (2013.01); *G01N 33/54366* (2013.01); *G01N 33/54393* (2013.01); *G01N 2035/00158* (2013.01); *G01N 2035/00495* (2013.01)

(58) Field of Classification Search
CPC .. C12Q 1/6837; C12Q 1/6834; C12Q 1/6813; C12Q 1/68; C12Q 1/6802; G01N 33/54393; G01N 33/543; G01N 33/53; G01N 33/50; G01N 3/165; G01N 3/16; G01N 3/00; G01N 33/00; B01F 9/0003; B01F 9/00
USPC ......... 436/501; 422/506, 504, 502, 501, 500
See application file for complete search history.

(56) References Cited

U.S. PATENT DOCUMENTS 6,309,875 B1  10/2001  Gordon
2010/0091604 A1  4/2010  Jesson

FOREIGN PATENT DOCUMENTS

EP  2 410 341  1/2012
JP  2003-339375  12/2003
(Continued)

*Primary Examiner* — Christine T Mui
(74) *Attorney, Agent, or Firm* — DLA Piper LLP (US)

(57) ABSTRACT

A method of stirring a test substance-containing solution injected into an analysis chip, wherein said analysis chip includes a recess to which said test substance-containing solution is injected; and a selective binding substance, which selectively binds to said test substance, is immobilized on the entirety or a part of the bottom surface of said recess, said method including injecting said test substance-containing solution to the space in said recess of said analysis chip such that said space is partially left unfilled; and rotating said analysis chip to which said test substance-containing solution is injected applying a centrifugal acceleration of not less than 1×g.

12 Claims, 7 Drawing Sheets

(56) References Cited

FOREIGN PATENT DOCUMENTS

| | | |
|---|---|---|
| JP | 2005/229934 | 9/2005 |
| JP | 2007/285828 | 11/2007 |
| JP | 2010-519536 | 6/2010 |
| JP | 4473007 | 6/2010 |
| WO | 2005/090997 | 9/2005 |
| WO | 2010/106989 | 9/2010 |

SEQUENCE LISTING

<160> NUMBER OF SEQ ID NOS: 9

<210> SEQ ID NO 1
<211> LENGTH: 69
<212> TYPE: DNA
<213> ORGANISM: Homo sapiens

<400> SEQUENCE: 1
tgaagagggg aggggcctag ggagccgcac cttgtcatgt accatcaata aagtaccctg    60
tgctcaacc                                                            69

<210> SEQ ID NO 2
<211> LENGTH: 69
<212> TYPE: DNA
<213> ORGANISM: Homo sapiens

<400> SEQUENCE: 2
aactagctgc caaacaactt caaccgtgt aattcatgta catttgcaac agccagcccg     60
gtacagcct                                                            69

<210> SEQ ID NO 3
<211> LENGTH: 70
<212> TYPE: DNA
<213> ORGANISM: Homo sapiens

<400> SEQUENCE: 3
gctgctttct gaccaaatgt ttttccatct gtgtacagct ccagctgttt gaagagaggg    60
aacaacacgg                                                           70

<210> SEQ ID NO 4
<211> LENGTH: 69
<212> TYPE: DNA
<213> ORGANISM: Homo sapiens

<400> SEQUENCE: 4
gaagggctcg catcatccag gaaagaattc agcagaagtt cacttttttt cttattcaaa    60
gagtctgga                                                            69

<210> SEQ ID NO 5
<211> LENGTH: 30
<212> TYPE: DNA
<213> ORGANISM: Human papillomavirus type 16

<400> SEQUENCE: 5
atccgtaact acatcttcca catacaccaa                                     30

<210> SEQ ID NO 6
<211> LENGTH: 20
<212> TYPE: DNA
<213> ORGANISM: Human papillomavirus
<220> FEATURE:
<221> NAME/KEY: misc_feature
<222> LOCATION: (1)..(1)
<223> OTHER INFORMATION: biotynylated base
<220> FEATURE:
<221> NAME/KEY: misc_feature
<222> LOCATION: (20)..(20)
<223> OTHER INFORMATION: biotynylated base

<400> SEQUENCE: 6
gcacagggac ataaaaatgg                                                20

```
<210> SEQ ID NO 7
<211> LENGTH: 25
<212> TYPE: DNA
<213> ORGANISM: Human papillomavirus
<220> FEATURE:
<221> NAME/KEY: misc_feature
<222> LOCATION: (1)..(1)
<223> OTHER INFORMATION: biotinylated base
<220> FEATURE:
<221> NAME/KEY: misc_feature
<222> LOCATION: (25)..(25)
<223> OTHER INFORMATION: biotinylated base

<400> SEQUENCE: 7
gaaaaataaa ctgtaaatca tattc                                   25

<210> SEQ ID NO 8
<211> LENGTH: 23
<212> TYPE: DNA
<213> ORGANISM: Human papillomavirus
<220> FEATURE:
<221> NAME/KEY: misc_feature
<222> LOCATION: (1)..(1)
<223> OTHER INFORMATION: biotinylated base
<220> FEATURE:
<221> NAME/KEY: misc_feature
<222> LOCATION: (23)..(23)
<223> OTHER INFORMATION: biotinylated base

<400> SEQUENCE: 8
tttgttactg tggtagatac tac                                     23

<210> SEQ ID NO 9
<211> LENGTH: 20
<212> TYPE: DNA
<213> ORGANISM: Human papillomavirus
<220> FEATURE:
<221> NAME/KEY: misc_feature
<222> LOCATION: (1)..(1)
<223> OTHER INFORMATION: biotinylated base
<220> FEATURE:
<221> NAME/KEY: misc_feature
<222> LOCATION: (20)..(20)
<223> OTHER INFORMATION: biotinylated base

<400> SEQUENCE: 9
gatcagtatc caatdggacg                                         20
```

US 9,944,976 B2

METHOD FOR STIRRING SOLUTION

TECHNICAL FIELD

This disclosure relates to a method of stirring a solution containing a test substance, which method is used to bring a solution containing a test substance into contact with a substance that selectively binds to the test substance immobilized on a substrate (hereinafter, referred to as "selective binding substance") and allowing them to react with each other.

BACKGROUND

An analysis chip comprises a substrate on which a selective binding substance (such as a nucleic acid, a protein, a lipid or a saccharide) that selectively binds to a test substance is immobilized. The selective binding substance on the substrate and the test substance are allowed to undergo a hybridization reaction usually in a solution and, from the results of the reaction, the existence, condition, quantity or the like of a substance contained in the test substance are analyzed. As the substrate, a glass substrate, a metal substrate or a resin substrate is usually employed.

One example of an analysis chip is called "microarray" in which molecules such as DNAs, proteins or sugar chains are densely arranged on a substrate for the purpose of, for example, simultaneously assaying the expressions of numerous genes in the number of several tens to several tens of thousands. The use of microarray enables detection and quantification of nucleic acids based on nucleic acid-nucleic acid hybridization reaction or detection and quantification of proteins and sugar chains based on protein-protein, sugar chain-sugar chain or sugar chain-protein specific reaction so that systematic and comprehensive gene expression analysis can be carried out on, for example, various disease animal models and cell biological phenomena. Specifically, the functions of genes, that is, proteins encoded by the genes can be clarified, and the timing of the expression of the proteins as well as the places of their actions can be identified. By using a microarray to analyze variations in gene expression of organisms at the cell or tissue level and combining the data of physiological, cell biological and biochemical phenomena to construct a database for gene expression profiles, it becomes possible to search disease genes and therapy-related genes and to explore therapeutic strategies.

Among analysis chips, DNA microarrays (DNA chips) are used for detection, quantification and the like of nucleic acids based on nucleic acid-nucleic acid hybridization reaction. As a DNA chip, for example, a chip in which a large number of DNA fragments are densely arrayed and immobilized on a glass flat substrate is employed. Such a DNA chip is used to detect each gene contained in a sample or measuring the amount thereof by, for example, a method in which a sample prepared by labeling the genes expressed in a cell of interest or the like with a fluorescent dye or the like is subjected to hybridization to allow complementary nucleic acids (DNA or RNA) to bind with each other and the fluorescence of the binding sites is quickly detected using a high-resolution detection device (scanner), or a method of detecting a response such as electric current based on an electrochemical reaction. DNA chips have large expectations not only in gene expression analysis based on detection and quantification of expressed genes, but also in its application fields such as detection of single nucleotide polymorphisms (SNP) in genes.

In addition, analysis chips have been utilized as a means of examining and analyzing not only nucleic acids such as DNA, but also proteins and saccharides. Especially, in protein analysis chips, proteins such as antibodies, antigens and enzyme substrates are immobilized on a substrate.

WO 2005/090997 discloses a method of stirring a test substance-containing solution by rotating an analysis chip having an irregular structure and thereby allowing fine particles or air bubbles to move in the analysis chip. In that method, by allowing the fine particles or air bubbles to move without coming into contact with the surface immobilized with a selective binding substance, even with a trace amount of the test substance, good S/N ratio and strong fluorescence signal can be obtained.

JP 2007-285828 A discloses a method capable of carrying out a selective reaction between a test substance and a selective binding substance in a simple and stable manner by rotating an analysis chip having an irregular structure in the substantially horizontal direction and stirring the test substance solution using fine particles.

JP 2003-339375 A discloses a hybridization method and an apparatus in which, by rotating a container containing a sample solution and fine particles and allowing the fine particles to fall in the direction of gravity, the sample solution in the container is stirred.

Japanese Patent No. 4473007 discloses a hybridization method wherein a hybridization solution is injected into a special hybridization chamber in which a microarray is arranged such that the space thereof is partially left unfilled and the chamber is then rotated to shift the position of the space filled with the solution in the chamber, thereby stirring the solution.

U.S. Pat. No. 6,309,875 discloses a rotation-and-revolution type hybridization apparatus which stirs a sample solution by rotating the apparatus itself while revolving a microarray arranged on a turntable.

In the method of stirring a solution according to WO 2005/090997, the analysis chip is rotated at a relatively low rotation rate of, for example, 3 rpm and, in that case, the hybridization reaction requires 10 hours. Therefore, that method is not suitable for prompt detection of a test substance. In the same manner, the method of stirring a test substance solution according to JP 2007-285828 A is also not applicable to prompt detection of a test substance because the hybridization reaction in that method requires 16 hours. Further, although the method disclosed in JP 2003-339375 A is stated to have an effect of shortening the time required for hybridization, the hybridization reaction actually requires 6 hours. Therefore, it is difficult to apply that method to an analysis where prompt diagnosis is demanded. Moreover, in the hybridization method disclosed in Japanese Patent No. 4473007, although the CV value is improved by rotating the chamber as compared to when the reaction is carried out by simply leaving the hybridization solution, there is hardly any change in the signal intensity and the progress of the reaction is not accelerated. The apparatus disclosed in U.S. Pat. No. 6,309,875 is an apparatus which enables stirring of microarray with a small amount of sample solution. However, the time required for hybridization and shortening thereof are not mentioned and it is thus unclear if the apparatus is adaptable to prompt diagnosis.

The solution-stirring methods disclosed in WO 2005/090997, JP 2007-285828 A, JP 2003-339375 A, Japanese Patent No. 4473007 and U.S. Pat. No. 6,309,875 are all aimed at improving the detection sensitivity by increasing the efficiency of hybridization reaction. However, hybridization reactions in those methods actually require 6 to 20 hours. Thus, those methods cannot be viewed as technologies to dramatically improve the speed of detection or quantification of a test substance using an analysis chip. Therefore, until now, in the field of analysis of a test substance using an analysis chip where it is demanded to perform detection or quantification in a short time of several minutes to two hours at the most, for example, in the examination and diagnostic applications of infectious diseases such as influenza, sepsis and the like, there has not been presented a method of stirring a test substance solution which enables analysis to be performed with such a speed that satisfies the demand.

It could therefore be helpful to provide a means of accelerating the progress of selective binding reaction (hybridization reaction) between a selective binding substance immobilized on an analysis chip and a test substance, particularly a means of enabling analyzation of a test substance in a short time.

SUMMARY

We intensively studied the method of stirring a test substance-containing solution by which, in an analysis of a test substance using an analysis chip, the reaction between the test substance and an immobilized selective binding substance can be accelerated. We discovered that stable selective binding reaction can be realized in a short time by injecting the test substance-containing solution into a recess of the analysis chip such that the space of the recess is partially left unfilled and rotating the analysis chip applying a centrifugal acceleration of not less than 1×g to stir the solution.

We thus provide:

(1) A method of stirring a test substance-containing solution injected into an analysis chip, wherein the analysis chip comprises a recess to which the test substance-containing solution is injected; and a selective binding substance, which selectively binds to the test substance, is immobilized on the entirety or a part of the bottom surface of the recess, the method comprising: injecting the test substance-containing solution to the space in the recess of the analysis chip such that the space is partially left unfilled; and rotating the analysis chip to which the test substance-containing solution is injected applying a centrifugal acceleration of not less than 1×g.

(2) The method of stirring a solution according to (1), wherein the analysis chip to which the test substance-containing solution is injected is rotated with a rotation radius of 0.1 mm to 20 mm.

(3) The method of stirring a solution according to (1) or (2), wherein the test substance-containing solution is injected into the above-described recess such that 10% to 70% of the space is left unfilled.

(4) The method of stirring a solution according to any one of (1) to (3), wherein the above-described analysis chip comprises plural recesses to which the test substance-containing solution is injected, the plural recesses being separated by a wall(s) from one another.

(5) The method of stirring a solution according to any one of (1) to (4), wherein the above-described analysis chip is fitted with a cover that covers the entirety of the above-described recess(es); and the above-described test substance-containing solution is sealed in the recess(es).

(6) The method of stirring a solution according to any one of (1) to (5), wherein the analysis chip to which the test substance-containing solution is injected is arranged such that the bottom surface(s) of the above-described recess(es) is/are horizontal or substantially horizontal; and the analysis chip is rotated in the horizontal or substantially horizontal direction.

(7) A method of analyzing a test substance, the method comprising: allowing the test substance to bind to a selective binding substance immobilized on an analysis chip by the method of stirring a solution according to any one of (1) to (6); and detecting the test substance bound to the selective binding substance.

According to the test substance solution-stirring method, the selective reaction between a test substance and a selective binding substance immobilized on an analysis chip can be effectively accelerated and the chances of the selective binding substance and the test substance to come close with each other can be markedly increased. Therefore, it becomes possible to detect or quantify a test substance contained in a test substance solution using an analysis chip in a short period of time.

In addition, according to the test substance solution-stirring method, even when an analysis chip having a plurality of recesses to which a test substance-containing solution is injected is employed, since the solution in the respective recesses can be stirred under the same conditions, the reaction between the selective binding substance and the test substance in the respective recesses can also be performed under the same conditions so that occurrence of reaction variation among the recesses can be inhibited.

BRIEF DESCRIPTION OF THE DRAWINGS

FIG. 1(a) shows an example where the analysis chip has one recess; FIG. 1(b) shows an example where the analysis chip has a plurality of recesses; and FIG. 1(c) is a cross-sectional view of a recess.

FIG. 2(a) shows an example where the analysis chip has one recess; FIG. 2(b) shows an example where the analysis chip has a plurality of recesses; and FIG. 2(c) is a cross-sectional view of a recess.

FIG. 3(a) shows an example where the analysis chip has one recess; FIG. 3(b) shows an example where the analysis chip has a plurality of recesses; and FIG. 3(c) is a cross-sectional view of a recess.

FIG. 4(a) shows an example where the analysis chip has one recess; FIG. 4(b) shows an example where the analysis chip has a plurality of recesses; and FIG. 4(c) is a cross-sectional view of a recess.

FIG. 5(a) shows a recess having a hexagonal bottom; FIG. 5(b) shows a recess having a tetragonal bottom with rounded corners; and FIG. 5(c) shows recess having an elliptical bottom.

DESCRIPTION OF SYMBOLS

Figure 1A:
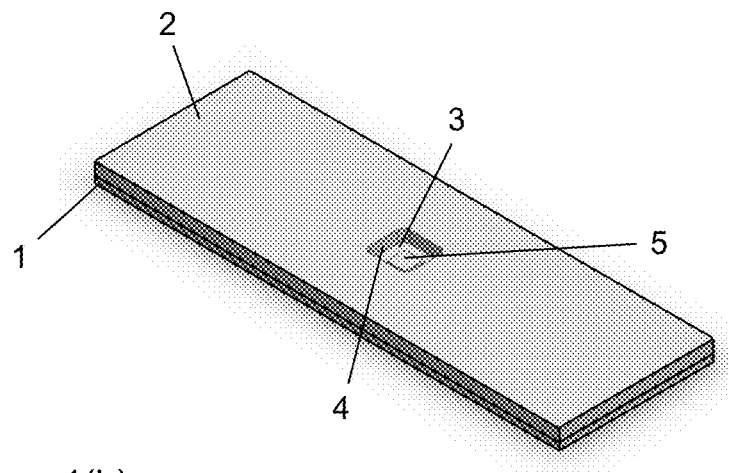
FIGS. 1(a)-1(c) show examples of our analysis chips.

1: Substrate
2: Plate material having a through-hole(s)
3: Bottom surface of recess
4: Wall surface of recess
5: Selective binding substance-immobilized surface
6: Recess (or space of recess)
7: Cover
8: Injection hole
9: Space (or air bubble) not filled with solution
10: Analysis chip

DETAILED DESCRIPTION

The term "analysis chip" refers to a chip to which a test substance-containing solution (hereinafter, may also be referred to as "test substance solution") is injected for the purpose of detecting the existence of a test substance and measuring the amount, properties and the like of the test substance. Specific examples thereof include biochips to measure the amount or existence of a test substance based on the reaction between a selective binding substance immobilized on the carrier surface and the test substance. More specific examples include DNA chips in which nucleic acids are immobilized on the carrier surface; protein chips in which proteins represented by antibodies are immobilized on the carrier surface; sugar chain chips in which sugar chains are immobilized on the carrier surface; and cell chips wherein cells are immobilized on the carrier surface.

On the analysis chip, a recess(es) to which a test substance-containing solution is injected is/are formed. Each recess forms a space constituted of a wall surface and a bottom surface, and a selective binding substance is immobilized on the entirety or a part of the bottom surface of the recess.

Examples of our analysis chips will now be described referring to FIGS. 1 to 6.

Figure 1B:
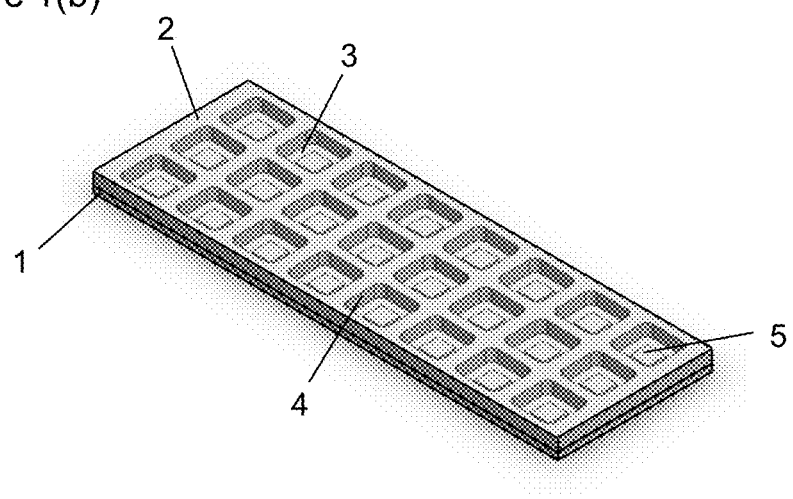
Figure 1C:
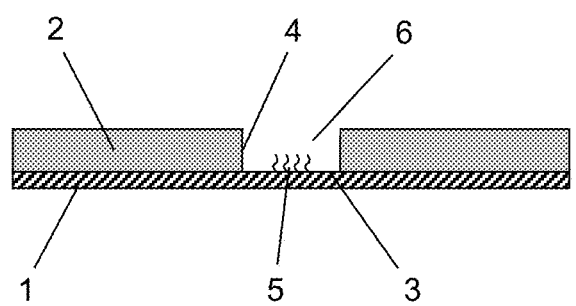

FIG. 1 illustrates analysis chips constituted of a flat substrate 1 (e.g., a glass slide) and a plate material 2 having a through-hole(s). The substrate 1 and the plate material 2 having a through-hole(s) are joined to form a recess 6(s) (or a recess space(s)) constituted of a wall surface 3 and a wall surface 4. FIG. 1(a) shows an example where the analysis chip has one recess 6; FIG. 1(b) shows an example where the analysis chip has a plurality of recess 6s; and FIG. 1(c) is a cross-sectional view of each recess. A selective binding substance is immobilized on a part of the surface (upper surface) of the substrate 1, and this surface forms a selective binding substance-immobilized surface 5 on a part of the bottom surface 3 of each recess 6 when the substrate 1 and the plate material 2 are joined.

In such an analysis chip as shown in FIG. 1 constituted of a flat substrate on which a selective binding substance is immobilized and a plate material comprising a through-hole(s) for the formation of a recess(es), the material of the flat substrate and that of the plate material are not particularly restricted and, for example, an inorganic material such as glass, ceramic or silicon, or a polymeric material such as polyethylene terephthalate, cellulose acetate, polycarbonate, polystyrene, polymethyl methacrylate or silicone rubber, can be preferably used. The method of joining the flat substrate and the plate material is also not particularly restricted, and the flat substrate and the plate material may be adhered using an adhesive in a substantially undetachable manner or may be adhered via a double-sided adhesive tape or an adhesive layer made of a resin composition or the like in a detachable manner. Further, the number of recesses per analysis chip can be set in accordance with the purpose of the analysis, and one or a plurality of recesses can be formed.

Figure 2A:
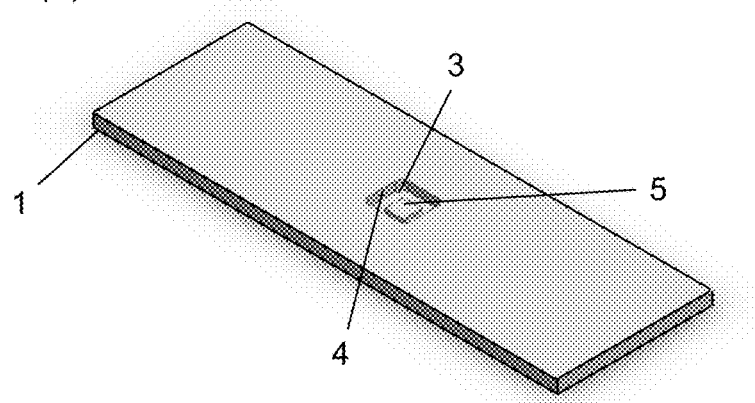
FIGS. 2(a)-2(c) show examples of our analysis chips.
Figure 2B:
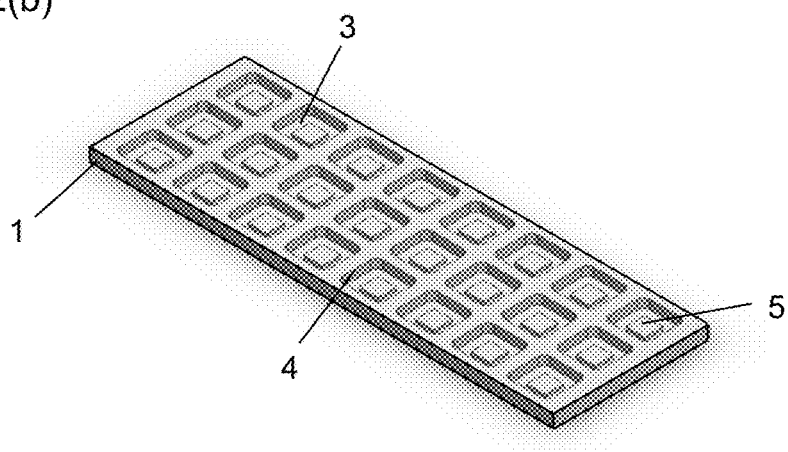
Figure 2C:
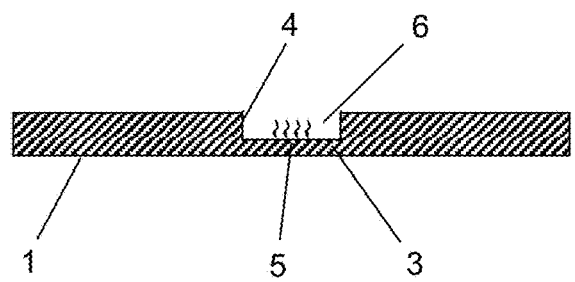
Figure 3A:
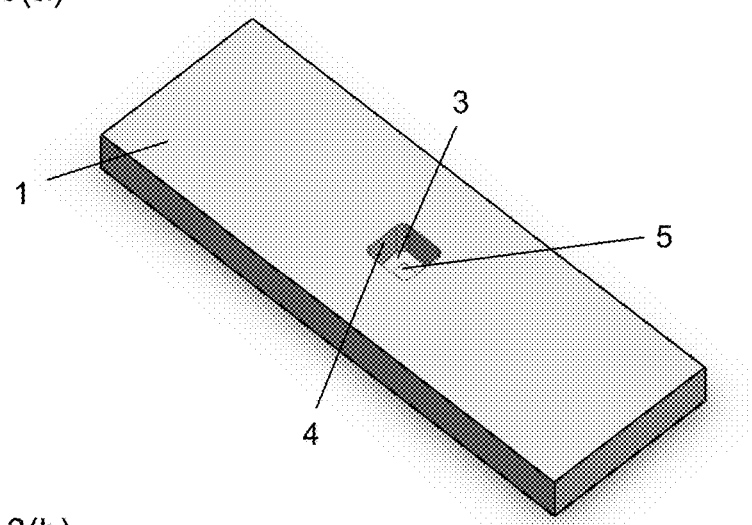
FIGS. 3(a)-3(c) show examples of our analysis chips.
Figure 3B:
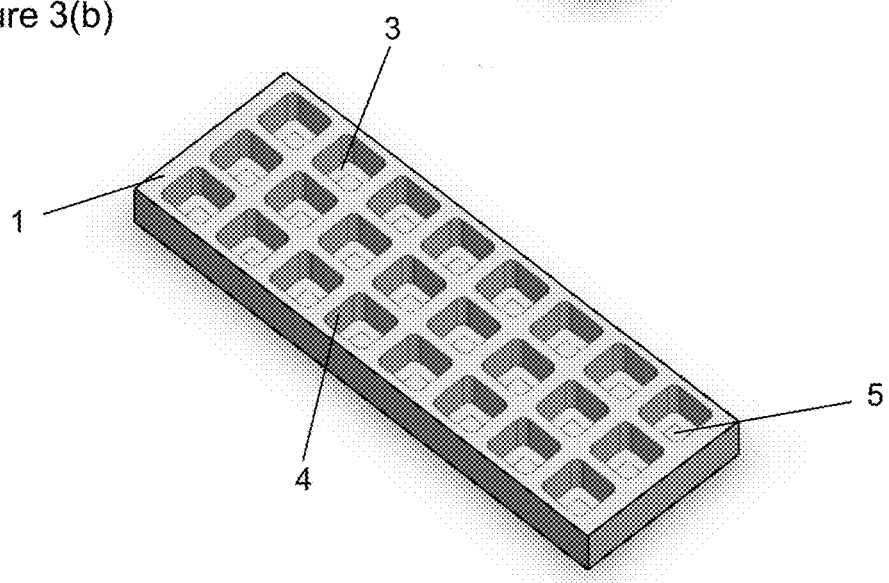
Figure 3C:
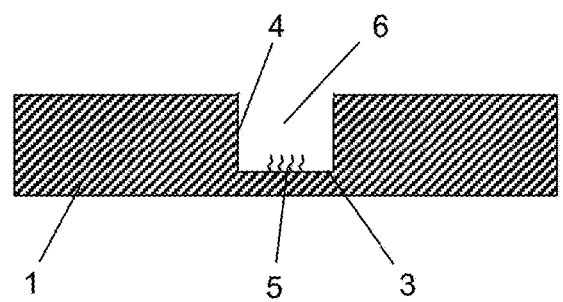

FIGS. 2 and 3 show analysis chips in which a recess 6(s) is/are formed on the substrate 1 by, for example, injection molding, without using the plate material having a through-hole(s) shown in FIG. 1. Each recess 6 formed on the substrate 1 comprises a space constituted by the bottom surface 3 and the wall surface 4, and a part of the bottom surface 3 of the recess is the selective binding substance-immobilized surface 5. FIGS. 2(a) and 3(a) each show an example where the analysis chip has one recess; FIGS. 2(b) and 3(b) each show an example where the analysis chip has a plurality of recesses; and FIGS. 2(c) and 3(c) each show an example of the recess cross section. The number of recesses per analysis chip can be arbitrarily selected in accordance with the purpose of the analysis.

In the analysis chips shown in FIGS. 2 and 3, as the material of the substrate, the same material as that of the substrate of the above-described analysis chips shown in FIG. 1 can be used.

In the analysis chip used in the method of stirring a solution, the depth of the recess(es) is not particularly restricted. However, it is preferably 0.1 to 10 mm, more preferably 0.5 to 5 mm. FIG. 2 shows embodiments of the analysis chip of a type having a shallow recess 6(s) and FIG. 3 shows examples of the analysis chip of a type a deep recess 6(s).

When the analysis chip to which a test substance solution is injected is rotated, when such an analysis chip having a deep recess(es) as shown in FIG. 3 is used, the analysis chip can be rotated as is, without fitting a cover thereon. Meanwhile, when such an analysis chip having a shallow recess(es) as shown in FIG. 2 is used, it is preferred that a cover which covers the entirety of the recess(es) be fitted to seal the test substance solution in the recess(es). For example, when the depth of the recess(es) is 5 mm or less, it is preferred that a cover be fitted in accordance with the rotation conditions of the analysis chip (centrifugal acceleration, rotation rate and rotation radius).

Figure 4A:
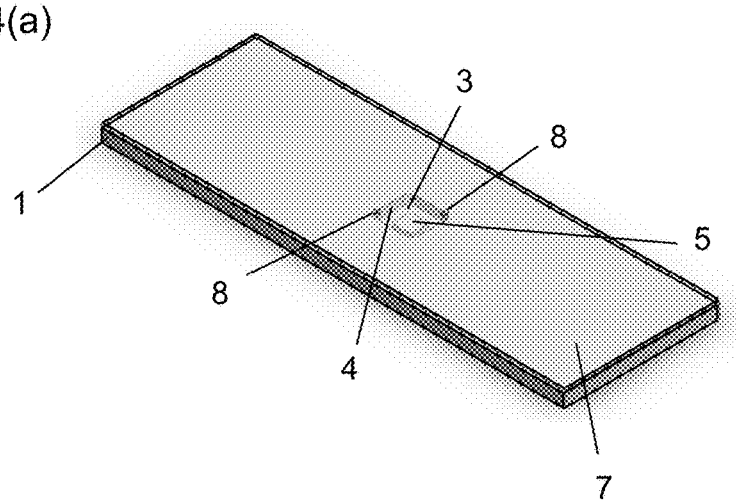
FIGS. 4(a)-4(c) show examples where our analysis chips are fitted with a cover.
Figure 4B:
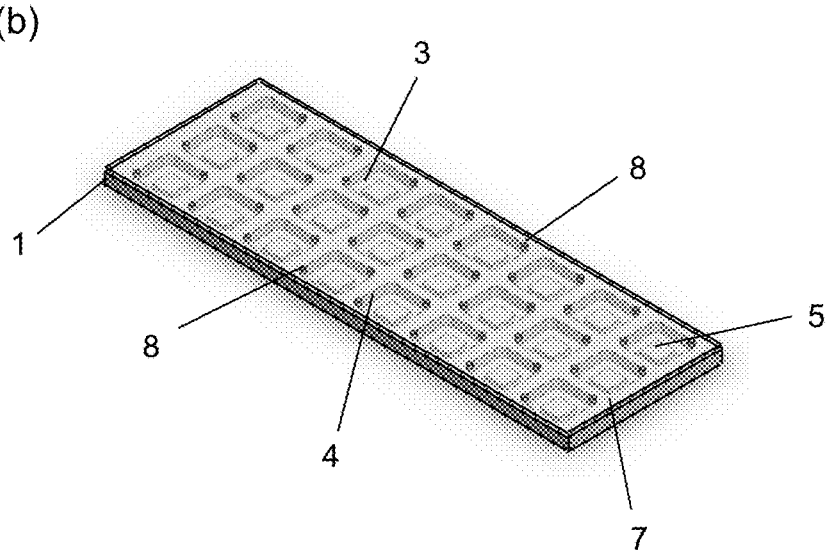
Figure 4C:
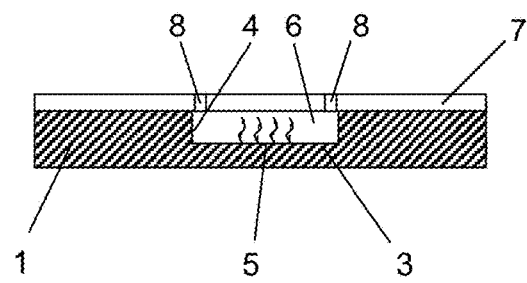

FIG. 4 shows examples where the analysis chip is fitted with a cover 7, which covers the entirety of the recess 6(s), and the test substance solution is sealed in the recess 6(s). More specifically, FIG. 4 shows examples where the analysis chip shown in FIG. 2 or 3 is fitted with the flat-plate cover 7. FIG. 4(a) shows an example where the analysis chip has one recess; FIG. 4(b) shows an example where the analysis chip has a plurality of recesses; and FIG. 4(c) is a cross-sectional view of a recess. In these examples, the cover 7 comprises injection hole 8s to inject a test substance solution into the recess(es).

As the cover, a flat plate made of a resin, rubber, glass or the like, or a sealing material such as an adhesive tape can be used. By providing the cover with an injection hole(s) to inject a test substance solution into the recess(es), the cover can be fitted before the test substance solution is injected into the recess. In this case, it is preferred that the cover have a plurality of injection holes and, for example, 2 to 4 injection holes can be formed per recess. Meanwhile, when the cover is fitted after the test substance solution is injected, an injection hole may or may not be formed on the cover and, for example, a method of covering and sealing the opening with an adhesive tape, a method of sealing the opening by bringing a plate material on which an O-ring conforming to the shape of the opening is fixed into close contact with the opening, or a method of covering and sealing the opening with a clay-like substance can be suitably employed.

When performing hybridization reaction and when it is necessary to prevent evaporation of the test substance solution or to strictly maintain the reaction temperature constant, it is preferred that the recess space(s) of the analysis chip be sealed and, in this case, it is preferred that the analysis chip be fitted with a cover.

Figure 5A:
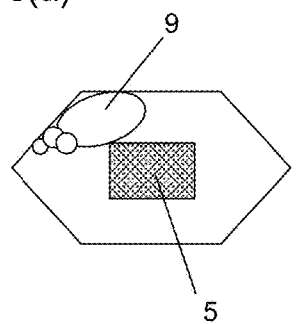
FIGS. 5(a)-5(c) illustrate top views showing examples of preferred shapes of the bottom surface of a recess of an analysis chip.
Figure 5B:
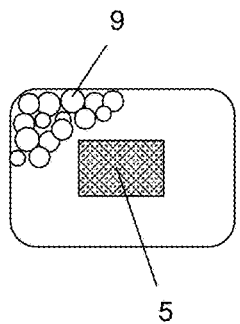
Figure 5C:
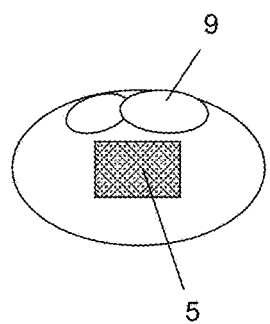

In the analysis chip used in the method of stirring a solution, it is preferred that the bottom surface of each recess have such a shape that allows the space (or air bubble) in the recess left unfilled with the test substance solution to move easily when the analysis chip is rotated. For example, as shown in FIG. 5, it is preferred to use an analysis chip in which the bottom surface of each recess has (a) a hexagonal shape, (b) a tetragonal shape or (c) an elliptical shape, since this allows a space (or air bubble) 9 remaining in the recess to move easily. Further, when the bottom surface of each recess has a polygonal shape, it is preferred that the corners thereof be rounded (for example, as in FIG. 5(b)) since this also allows the space (or air bubble) in the recess left unfilled with the test solution to move easily.

Figure 6:
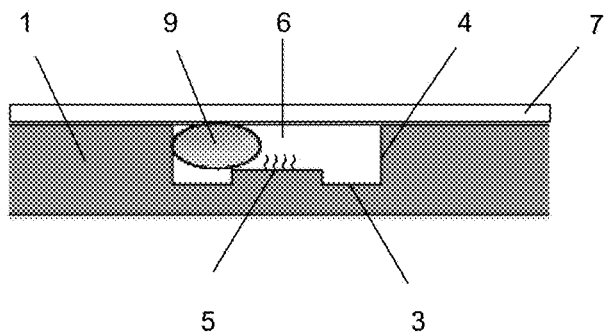
FIG. 6 is a cross-sectional view of an analysis chip which shows an example where a test substance-containing solution is injected to the analysis chip.

FIG. 6 is a cross-sectional view taken in the vicinity a recess of the analysis chip, which shows an example where a test substance-containing solution is injected to the analysis chip fitted with the cover. It illustrates a condition where a test substance-containing solution is injected to the space 6 in the recess of the analysis chip; a space (or air bubble) 9, which is not filled with the solution, is formed; and the cover 7 is fitted. By rotating the analysis chip in the condition shown in FIG. 6, the test substance solution can be stirred to perform hybridization reaction.

The term "selective binding substance" means a substance that can selectively bind to a test substance directly or indirectly. Representative examples of the selective binding substance that can bind to the surface of a carrier include nucleic acids, proteins, peptides, saccharides and lipids.

Examples of the nucleic acids include DNAs and RNAs, and the nucleic acid may also be PNA or LNA. Examples of DNAs that can be used include, but not limited to, chromosomal DNAs, viral DNAs and DNAs of bacteria, mold and the like, as well as cDNAs obtained by reverse transcription of RNAs, and partial fragments of these DNAs. Further, examples of RNAs that can be used include, but not limited to, messenger RNAs, ribosomal RNAs, small RNAs, micro RNAs, and partial fragments of these RNAs. In addition, chemically synthesized DNAs, RNAs and the like are also included in the examples. A single-stranded nucleic acid having a specific base sequence selectively hybridizes and binds with a single-stranded nucleic acid having a base sequence that is complementary to the specific base sequence or to a part thereof. Therefore, such a single-stranded nucleic acid also corresponds to the "selective binding substance" defined herein. The nucleic acid may be one derived from a natural product such as a living cell, or may be one synthesized using a nucleic acid synthesizer. Preparation of DNA or RNA from a living cell can be carried out by a know method. For example, DNA can be extracted by the method of Blin et al. (Blin et al., Nucleic Acids Res. 3:2303 (1976)) or the like and RNA can be extracted by the method of Favaloro et al. (Favaloro et al., Methods Enzymol. 65:718 (1980)) or the like. As the nucleic acid to be immobilized, for example, a linear or circular plasmid DNA or chromosomal DNA, a DNA fragment obtained by cleaving these DNAs with a restriction enzyme or by chemical cleavage of these DNAs, a synthetic DNA prepared in vitro using an enzyme or the like, or a chemically synthesized oligonucleotide can also be used.

Examples of the proteins include antibodies, antigen-binding fragments of antibodies such as Fab fragments and F(ab')2 fragments, and various antigens. An antibody or antigen-binding fragment thereof selectively binds to its corresponding antigen and an antigen selectively binds to its corresponding antibody. Therefore, they also correspond to the "selective binding substance".

Examples of the saccharides include various monosaccharides and sugar chains such as oligosaccharides and polysaccharides.

Examples of the lipids include simple lipids and complex lipids.

Further, an antigenic substance other than the above-described nucleic acids, proteins, saccharides and lipids may be immobilized as well. Moreover, as the selective binding substance, cells may also be immobilized on the carrier surface.

Among these selective binding substances, particularly preferred ones include DNAs, RNAs, proteins, peptides, saccharides, sugar chains and lipids.

Examples of the test substance include, but not limited to, nucleic acids to be measured (target nucleic acids), such as genes of pathogenic bacteria, viruses and the like, causative genes of hereditary diseases, and parts thereof; various antigenic biological components; and antibodies against pathogenic bacteria, viruses and the like.

In the method of stirring a solution, examples of the solutions containing these test substances that may be used include, but not limited to, body fluids such as blood, serum, plasma, urine, feces, spinal fluid, saliva and various tissue fluids; various foods and beverages; and dilutions thereof. The viscosity of the test substance-containing solution is not particularly restricted as long as the recess space(s) of the analysis chip not filled with the test substance solution is/are movable when the analysis chip is rotated applying centrifugal acceleration.

The nucleic acid used as the test substance may be one which is extracted from blood or a cell by a conventional method and then labeled, or may be one which is amplified by a nucleic acid-amplification method such as PCR using the nucleic acid as a template. In the latter case, after carrying out the stirring method of the present invention, the measurement sensitivity can be largely improved. When an amplification product of a nucleic acid is used as the test substance, by carrying out the amplification in the presence of nucleoside triphosphate labeled with a fluorescent substance or the like, the resulting amplified nucleic acid can be labeled. Further, when the test substance is an antigen or an antibody, the antigen or the antibody used as the test substance may be directly labeled by a conventional method. Alternatively, a method in which, after allowing the antigen or the antibody which is the test substance to bind with a selective binding substance, the carrier is washed and a labeled antibody or antigen which undergoes antigen-antibody reaction with the antigen or antibody is allowed to react, followed by measurement of the label bound to the carrier, may also be employed. Moreover, when an unamplified nucleic acid is used as the test substance, for example, a method in which, after removing the 5'-end phosphate group of the nucleic acid with alkaline phosphatase, the test substance labeled with a fluorescent substance is allowed to react with a selective binding substance and the bound label is then measured, or a method in which, after capturing the test substance using a selective binding substance (capturing probe), a detection probe labeled with a fluorescent substance or the like is allowed to bind to the test substance and the label of the detection probe is then measured (sandwich hybridization method), can be preferably employed.

In the method of stirring a solution, a test substance subjected to the above-described labeling, amplification and the like is dissolved in an aqueous solution, an appropriate buffer or the like to prepare a test substance-containing solution (test substance solution).

In the method of stirring a solution, the test substance solution is injected to the recess space(s) of the analysis chip in such a manner that the recess space(s) is/are partially left unfilled so that a space not filled with the test substance solution is formed in the recess(es). By not completely filling the recess space(s) with the test substance solution to form a space not filled with the test substance solution, the unfilled space moves within each recess when the analysis chip is rotated, thereby the test substance solution can be stirred. When the analysis chip is rotated, the unfilled space formed in each recess may exist as a single space, or may exist as a plurality of divided spaces, that is, as a plurality of air bubbles.

As for the ratio of the space not filled with the test substance solution with respect to the recess space(s), the lower limit thereof is preferably not less than 10%, more preferably not less than 20%, and the upper limit thereof is preferably not higher than 90%, more preferably not higher than 80%, still more preferably not higher than 70%. The ratio of the space unfilled with the test substance solution is preferably 10% to 90%, more preferably 15% to 80%, still more preferably 20% to 70%. When this ratio is less than 5%, the test substance solution does not sufficiently move within the recess space during the rotation of the analysis chip, so that the test substance solution may not be substantially stirred. Meanwhile, when the ratio is higher than 90%, the chance of the test substance-containing solution to come into contact with the region where the selective binding substance is immobilized is reduced, which impedes the reaction progress. Further, when such an analysis chip having a deep recess(es) as shown in FIG. 3 is rotated without fitting a cover thereon, the ratio of the space unfilled with the test substance solution is, for example, preferably 30% to 90%, more preferably 40% to 80%.

In the method of stirring a solution, the analysis chip to which a test substance-containing solution is injected is subjected to rotation to stir the solution. The term "rotation" used herein means that the analysis chip itself is rotated around a rotation axis by circular motion or elliptic motion. More particularly, the term "rotation" refers to a mode of rotation which is carried out such that circular motion having the same radius with a unique rotation center and the same radius is observed for any arbitrary point on the analysis chip.

Figure 7:
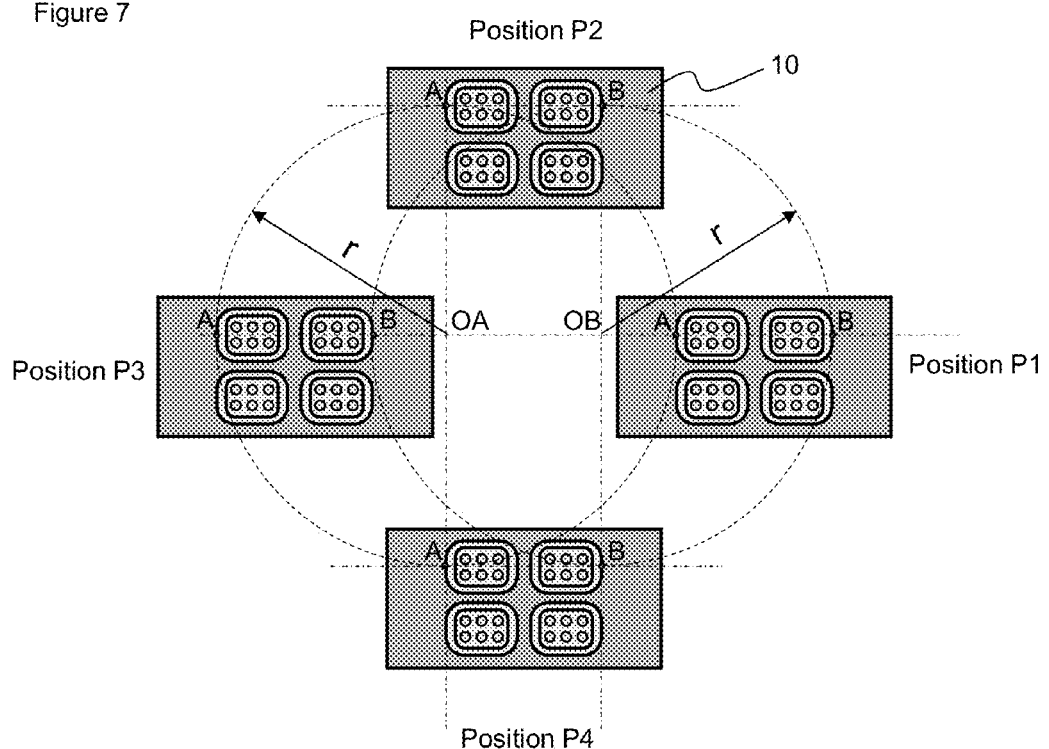
FIG. 7 is a drawing which illustrates chip rotation.
Figure 8:
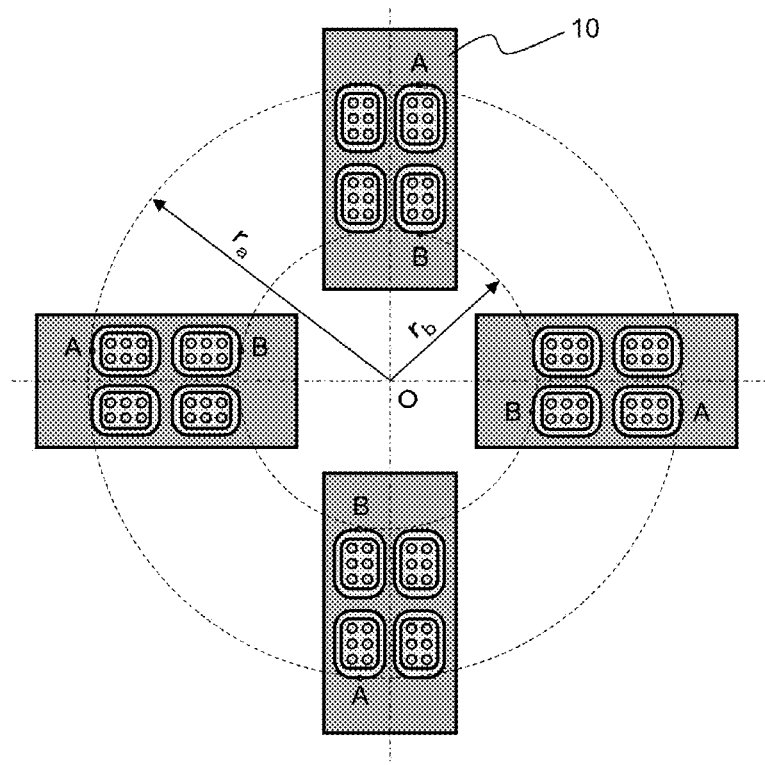
FIG. 8 is a drawing which illustrates a mode of rotation including the revolution.

FIG. 7 shows one example of the rotation according to the present invention. With regard to arbitrary points A and B on an analysis chip 10, the point A rotates at a prescribed rotation rate on a circular orbit having its center at OA and a radius, r. In the same manner, the point B also rotates at a prescribed rotation rate on a circular orbit having its center at OB and a radius, r. In this case, the straight lines AB connecting the arbitrary points A and B on the analysis chip are always parallel in an arbitrary orbit of the circular motion. For instance, in FIG. 7, even when the analysis chip 10 is located at any one of the positions P1, P2, P3 and P4, the straight lines AB are parallel to each other. Meanwhile, when the rotation mode includes revolution such as orbital rotation or rotary revolution, as shown in FIG. 8, the distances between the revolution center, O, and the respective arbitrary points A and B on the analysis chip 10 ($r_a$, $r_b$) are different. That is, in the rotation mode including revolution, the rotation radius of the circular motion varies depending on the position on the analysis chip.

When the analysis chip is rotated, it is preferred that the analysis chip be arranged such that its surface on which a selective binding substance is immobilized is parallel or substantially parallel to the rotation plane.

When an analysis chip having a plurality of recesses to which the test substance-containing solution is injected is used, since the solution in the respective recesses can be stirred under the same conditions by rotating the analysis chip, the reaction between the selective binding substance and the test substance in the respective recesses can also be performed under the same conditions so that the reaction variation among the recesses can be preferably reduced. Meanwhile, when the stirring is carried out by a rotation-revolution method in which the analysis chip is rotated while being revolved or a revolution method in which the rotation center is located outside the analysis chip, since the plurality of recesses are each stirred under different conditions, variations in the reaction may occur among the recesses.

The direction of the rotation plane in the rotation of the analysis chip is not particularly restricted and the analysis chip can be rotated, for example, in the horizontal or substantially horizontal direction, in the direction tilted by 15° from the horizontal direction, in the direction tilted by 30° from the horizontal direction, in the direction tilted by 45° from the horizontal direction, in the direction tilted by 60° from the horizontal direction, in the direction tilted by 75° from the horizontal direction, or in the vertical or substantially vertical direction. The direction of the rotation plane is preferably the horizontal or substantially horizontal direction. The term "substantially horizontal direction" means a direction that is nearly horizontal to the surface of the analysis chip on which a selective binding substance is immobilized and it is preferably, for example, a direction tilted by a range of 0° to 3° with respect to the horizontal plane. Further, the term "substantially vertical direction" means a direction that is nearly vertical to the surface of the analysis chip on which a selective binding substance is immobilized and it is preferably, for example, a direction tilted by a range of 0° to 3° with respect to the vertical plane.

The analysis chip may be rotated at a constant rotation rate or at varying rotation rates. Alternatively, the analysis chip may be rotated intermittently by, for example, stopping the rotation for a certain period of time. Further, the direction of the rotation is not particularly restricted and it may be clockwise or counterclockwise, or a combination thereof.

The time of rotating the analysis chip for performing the reaction is not particularly restricted and it can be appropriately determined within such a range that is sufficient for allowing the selective binding substance and the test substance to react with each other. For example, when the test substance is a nucleic acid, the time of the rotation can be set in accordance with the time required for hybridization reaction to take place between the nucleic acid and a probe nucleic acid that is the selective binding substance. The method of stirring a solution is characterized in that, by applying a centrifugal acceleration of not less than 1×g at the time of rotating the analysis chip, the selective reaction between the test substance and the selective binding substance can be effectively accelerated and the test substance can thus be detected or quantified in a short time. By taking advantage of this characteristic feature, particularly in cases where prompt detection or quantification is demanded such as when the analysis chip is used in an examination/diagnostic application, it is preferred that the analysis chip be rotated for a short time. For example, in the case of hybridization of nucleic acids, the reaction time is preferably 3 hours to 4 hours, more preferably 2 hours or shorter, still more preferably 1 hour or shorter, particularly preferably 0.5 hour or shorter.

Generally speaking, the centrifugal acceleration represents, in a rotationally moving system, the size of centrifugal force applied to an object in the form of acceleration and the centrifugal acceleration is proportional to the absolute value of the distance from the rotation center and the square of the angular velocity of the rotational motion. The centrifugal acceleration means a centrifugal force, that is, a relative centrifugal force (RCF), and it is calculated by Equation 1.

$$RCF = 1{,}118 \times R \times N^2 \times 10^{-8} \qquad (1)$$

RCF: relative centrifugal force (×g)
R: rotation radius (cm)
N: rotation rate (rpm)

In the method of stirring a solution, a centrifugal acceleration of not less than 1×g is applied when the analysis chip is rotated. The lower limit of the centrifugal acceleration is preferably not less than 5×g, more preferably not less than 10×g. The upper limit of the centrifugal acceleration is not particularly restricted. However, it is preferably 50×g or less, more preferably 40×g or less, still more preferably 30×g or less. The centrifugal acceleration is preferably 1×g to 50×g, more preferably 5×g to 40×g, still more preferably 10×g to 30×g.

In the method of stirring a solution, the desired centrifugal acceleration can be applied by appropriately setting the rotation rate and the rotation radius when rotating the analysis chip. Therefore, the rotation rate and the rotation radius can be selected in accordance with the specifications of the stirring apparatus used for stirring the analysis chip. For example, when the rotation radius is small, a large centrifugal acceleration can be imparted by increasing the rotation speed.

The value of the rotation radius can be appropriately selected in combination with the rotation rate such that the desired centrifugal acceleration is attained. The lower limit of the rotation radius is preferably not smaller than 0.1 mm, more preferably not smaller than 0.2 mm, still more preferably not smaller than 0.3 mm. Further, the upper limit of the rotation radius is preferably 20 mm or smaller, more preferably 10 mm or smaller, still more preferably 5 mm or smaller. The rotation radius is thus in the range of preferably 0.1 to 20 mm, more preferably 0.2 to 10 mm, still more preferably 0.3 to 5 mm. When the rotation radius is larger than 20 mm, since the centrifugal force is predominant, the space not filled with the test substance solution tends to be pushed against the periphery of the recess so that the stirring efficiency may be reduced and variations in the stirring may occur within a recess. Meanwhile, when the rotation radius is smaller than 0.1 mm, since the force acting in the direction of the rotation is predominant, the space not filled with the test substance solution tends to remain in the central part of the recess, so that the stirring efficiency may be reduced and variations in the stirring may occur.

Further, the value of the rotation rate can also be appropriately selected in combination with the rotation radius such that the desired centrifugal acceleration is attained, and it is preferably 500 rpm to 10,000 rpm, more preferably 750 rpm to 8,000 rpm. The smaller the rotation radius, the more preferred it is, and this is because the reaction apparatus and the stirring apparatus can be downsized and the apparatus for realizing the method of stirring a solution can thus be made compact.

When the analysis chip is rotated without fitting a cover thereon, to prevent spilling of the injected test substance solution, a stirring apparatus having a small rotation radius is preferably employed. For example, the rotation radius is preferably 0.1 mm to 5 mm, more preferably 0.2 mm to 4 mm, still more preferably 0.3 mm to 3 mm.

The stirring apparatus that stirs the analysis chip is not particularly restricted as long as it is capable of providing a centrifugal acceleration of not less than 1×g by a combination of the rotation rate and the rotation radius. As a commercially available product, a plate shaker can be preferably employed, and examples thereof include: "BioShake 5000 elm", "BioShake 3000-T elm" and "BioShake 3000 elm" (all of which are manufactured by Q. Instruments GmbH); "Monoshake", "Teleshake" and "Teleshake 1536" (all of which are manufactured by Thermo Fisher Scientific Inc.); "MS3 basic", "MS3 digital", "VXR basic Vibrax" (registered trademark) and "VORTEX 3" (all of which are manufactured by IKA); "Micro Plate Shaker N-704" (manufactured by Nissinrika Co., Ltd.); "Plate Shaker KM-M01" (manufactured by Kajixx Corporation); and "Plate Mixer P-10" (manufactured by Juji Field Inc.). When the stirring apparatus is integrated into an automated system, the apparatus is preferably one whose rotation rate, operation time and the like can be controlled from outside.

A stirring element may also be added to the space inside the recess(es). Examples of the stirring element include particles (beads) and microrods, and particles are particularly preferred. The shape of the particles and microrods is not particularly restricted as long as it allows the particles and microrods to move inside the recess(es) of the analysis chip and to thereby stir the test substance-containing solution. In the case of particles, they may have a spherical shape and a polygonal shape and, in the case of microrods, they may have an arbitrary shape such as a cylindrical shape or a prismatic shape. However, the stirring element preferably has a spherical shape. Further, the size of the particles is also not particularly restricted. However, for example, in the case of spherical particles, their diameter can be 0.1 μm to 1,000 μm and, in view of the stirring efficiency, the diameter is more preferably 50 μm to 500 μm. In the case of microrods, their length and bottom surface diameter can be preferably 50 μm to 5,000 μm and 10 μm to 300 μm, respectively. From the standpoint of the stirring efficiency and the like, a single type of particles or microrods can be selected for use, or two or more types of particles or microrods can be used in combination.

The material of the above-described particles and microrods is also not particularly restricted and, for example, glass, ceramics (e.g., yttria-partially-stabilized zirconia), metals (e.g., gold, platinum and stainless-steel) and plastics (e.g., nylons and polystyrenes) may be employed.

The analysis chip may also comprise a protrusion(s) to immobilize the selective binding substance on the upper surface thereof. By using an analysis chip having such a structure in the analysis of a test substance, when detecting a signal, the scanner can be focused on the upper surface of the protrusion(s) on which the selective binding substance is immobilized so that the detection noise can be largely reduced and the S/N ratio can be improved. Further, the analysis chip is preferably produced from a material capable of reducing autofluorescence and, for example, at least a part of the protrusion(s) on which the selective binding substance is to be immobilized is preferably black in color.

An index to indicate signal detection sensitivity, the S/N ratio (signal-to-noise ratio) can be used. In this case, it is preferred that the sensitivity be judged taking S/N=2 as the detection limit. In general, the concentration or amount of a test substance at which the S/N ratio becomes 2 to 3 is adopted as the detection limit and, when the S/N ratio is 2 or higher, it can be judged that reliable detection was attained at a level of the detection limit or higher (e.g., Makoto Niwa, "*Korenara Wakaru Kagakuno Tameno Toukei Shuhou—Tadashii Data no Atsukaikata—*", 2008, edited by Kagaku-Dojin Publishing Company, Inc., p. 101).

In the method of stirring a solution, since the progress of the selective reaction between a selective binding substance immobilized on the analysis chip and a test substance can be accelerated as compared to conventional methods, the test substance can be detected or quantified in a short time. For example, in hybridization of nucleic acids, the reaction time, which conventionally required 6 to 20 hours, can be largely shortened. Therefore, for example, when an analysis is performed using an analysis chip in the area of examination and diagnosis where a large number of samples are required to be analyzed promptly, it is preferred to employ the method of stirring a solution. The method of stirring a solution can be preferably used in the examination and diagnosis of infectious diseases such as influenza, sepsis and the like. Further, also when processing an enormous number of samples at an examination center, from the standpoint of cost reduction, the present invention is preferably applied since it enables to promptly perform the analysis.

EXAMPLES

Our methods will now be described in more detail by way of examples thereof. However, this disclosure is not restricted to the following examples.

Reference Example 1

(1) Preparation of Substrate of Analysis Chip

Using a known LIGA (Lithographie Galvanoformung Abformung) process, a mold for injection molding was prepared, and a substrate made of polymethyl methacrylate (PMMA), which had the below-described shape, was obtained by injection molding. The average molecular weight of the PMMA used here was 50,000 and carbon black (#3050B, manufactured by Mitsubishi Chemical Corporation) was incorporated into the PMMA in an amount of 1 wt % to make the resulting substrate black in color. When the spectral reflectance and the spectral transmission of the thus obtained black substrate were measured, the spectral reflectance was found to be 5% or less at any wavelength in the visible light range (wavelength of 400 nm to 800 nm) and the transmission was found to be 0.5% or less in the same wavelength range. Neither the spectral reflectance nor the spectral transmission had a particular spectral pattern (such as a peak) in the visible light range and the spectrum was uniformly flat. The spectral reflectance was measured for the light regularly reflected from the substrate using an apparatus (CM-2002, manufactured by Minolta Camera Co., Ltd.) equipped with an illumination light-receiving optical system in accordance with the Condition C of JIS Z8722.

The substrate used here had external dimensions of 76 mm in length, 26 mm in width and 1 mm in thickness and a recess of 6.48 mm in length, 6.90 mm in width and 0.12 mm in depth, in which recess 576 protrusions of 0.1 mm in diameter and 0.12 mm in height were formed (hereinafter, this substrate is referred to as "substrate A"). On this substrate A, the difference in height between the upper surfaces of the protrusions and the upper surface of the flat part was 3 μm or less. Further, the variation in the height of the upper surfaces of the protrusions was 3 μm or less and the protrusions were formed at a pitch of 0.18 mm.

The above-described substrate A was immersed in 10N aqueous sodium hydroxide solution for 12 hours at 70° C. The resulting substrate A was sequentially washed with pure water, 0.1N aqueous HCl solution and pure water, thereby generating carboxyl groups on the substrate surface.

(2) Immobilization of Selective Binding Substance

On the substrate A, oligonucleotides were immobilized as the respective selective binding substances (probe DNAs) under the following conditions. As the oligonucleotides corresponding to four genes of a to d, the oligonucleotides having the base sequences shown in SEQ ID NOs:1 to 4 (manufactured by Operon Biotechnologies Inc.; oligonucleotide set for DNA microarray, "*Homo sapience* (human) AROS V4.0 (60 bases each)") were employed. These oligonucleotides were each dissolved in pure water at a concentration of 0.3 nmol/μL to prepare stock solutions. When spotting the stock solutions on the substrate, they were each 10-fold diluted with PBS (prepared by dissolving 8 g of NaCl, 2.9 g of $Na_2HPO_4.12H_2O$, 0.2 g of KCl and 0.2 g of $KH_2PO_4$ altogether in pure water, adjusting the volume to 1 L and then adjusting the pH of the resulting solution to 5.5 with an addition of hydrochloric acid) to a final concentration of the probe DNA of 0.03 nmol/μL. In addition, in order to perform condensation between the carboxyl groups generated on the surface of the PMMA-made substrate and the terminal amino group of the probe DNA, 1-ethyl-3-(3-dimethylaminopropyl)carbodiimide (EDC) was added to a final concentration of 50 mg/mL. Then, using an arrayer (spotter) ("Gene Stamp-II", manufactured by Nippon Laser & Electronics Lab), the resulting solutions were spotted on the upper surfaces of the protrusions of the substrate A to prepare a substrate on which the probe corresponding to the gene a and having the base sequence shown in SEQ ID NO:1 was spotted at N=4 (hereinafter, referred to as "analysis chip 1") and a substrate on which the probes corresponding to the genes b to d and having the base sequences shown in SEQ ID NOs: 2 to 4 were each spotted at N=2 (hereinafter, referred to as "analysis chip 2"). Thereafter, the spotted substrates were each placed in a sealed plastic container and incubated under conditions of 37° C. and 100% humidity for about 20 hours. Finally, the resulting substrates were washed with pure water and dried by centrifugation using a spin dryer.

(3) Attachment of Cover Member to Analysis Chip Substrate

To each of the above-described analysis chips 1 and 2 immobilized with the selective binding substance(s), a cover member was attached as follows. The cover member was prepared by cutting a PMMA plate. On the thus obtained cover member, through-holes and liquid level-retaining chambers were formed. As an adhesive member, a double-sided adhesive tape was pasted on the cover member in such a manner that the tape was laminated along the fringe of the cover member at a thickness of 50 μm, and the cover member was then attached to the analysis chips 1 and 2.

(4) Preparation of Test Substance

The test substance was prepared using an aRNA (antisense RNA) commonly used as a test substance of microarray. From 5 μg of commercially-available total RNA derived from human cultured cells ("Human Reference RNA", manufactured by Clontech Laboratories, Inc.), an aRNA was prepared using an aRNA preparation kit manufactured by Ambion, "MessageAmp II aRNA Amplification Kit", and this aRNA was fluorescently labeled with Cy5 (manufactured by GE Healthcare) to obtain a Cy5-labeled aRNA.

(5) Reaction Solution for Hybridization between Selective Binding Substance and Test Substance In the following Examples and Comparative Examples, unless otherwise specified, a solution obtained by diluting the labeled aRNA prepared above with a hybridization solution containing 1-wt % BSA, 5×SSC, 0.01-wt % salmon sperm DNA and 0.1-wt % SDS (all of the concentrations are final concentrations) was used.

Example 1

Figure 9:
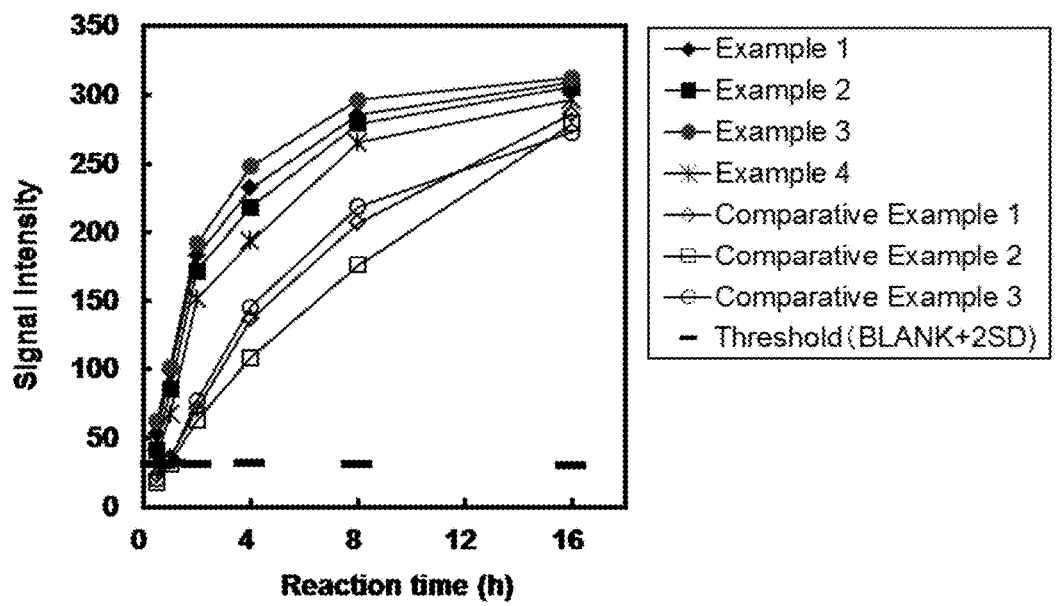
FIG. 9 is a graph showing the relationships between the reaction time and the signal intensity in Examples 1 to 4 and Comparative Examples 1 to 3.
Figure 10:
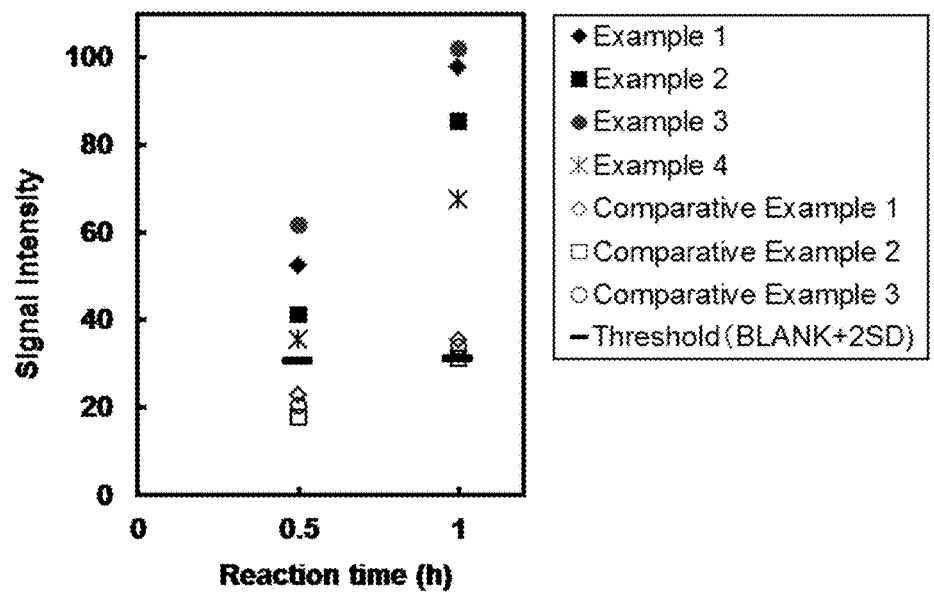
FIG. 10 is an enlarged graph which shows the part of the graph of FIG. 9 where the reaction time is 0 to 1 h.

To a solution containing 100 ng of the Cy5-labeled aRNA described in Reference Example 1, the hybridization solution was admixed to a volume of 25 μL to prepare a test substance solution. Then, 10 μL of the thus obtained test substance solution was injected to the analysis chip 1. The space of the recess that was not filled with the test substance solution had a volume of about 3 μL and the ratio of the space not filled with the test substance solution in the recess was about 23%. A total of 6 sets of the above-described analysis chip 1 were prepared. With the injection holes being sealed and the recess being thereby tightly closed, the analysis chips were set on a stirring apparatus "BioShake 5000" (manufactured by Q. Instruments GmbH; maximum rotation rate: 5,000 rpm, rotation radius: 0.6 mm), which was placed in an oven having a controlled temperature of 37° C. Then, the analysis chips were each stirred at 5,000 rpm for 0.5 h, 1 h, 2 h, 4 h, 8 h or 16 h to carry out reaction. In this process, a centrifugal acceleration of about 17.7×g was applied to each analysis chip. For each of the resulting analysis chips, the signal intensity (fluorescence intensity) of the hybridized labeled-aRNA was measured using a high-resolution fluorescence detector ("3D-Gene (registered trademark) Scanner", manufactured by Toray Industries, Inc.). The results thereof are shown in FIGS. 9 and 10 and Table 1. A signal having an intensity of the threshold value (blank spot average+2SD) or higher was detected 0.5 h after the start of the reaction; therefore, it was shown that the reaction proceeded rapidly.

Example 2

The test substance solution was injected to the analysis chip 1s (6 sets) in the same manner as in Example 1. The resulting analysis chips were set on a stirring apparatus "BioShake 5000", which was placed in an oven having a controlled temperature of 37° C., and then each stirred at 3,000 rpm for 0.5 h, 1 h, 2 h, 4 h, 8 h or 16 h to carry out reaction. In this process, a centrifugal acceleration of about 6.04×g was applied to each analysis chip. For each of the analysis chips, the signal intensity (fluorescence intensity) of the hybridized labeled-aRNA was measured using a high-resolution fluorescence detector. The results thereof are shown in FIGS. 9 and 10 and Table 1. A signal having an intensity of the threshold value or higher was detected 0.5 h after the start of the reaction. Therefore, it was shown that the reaction proceeded rapidly.

Example 3

The test substance solution was injected to the analysis chip 1s (6 sets) in the same manner as in Example 1. The resulting analysis chips were set on a stirring apparatus "MS3 digital" (manufactured by IKA; maximum rotation rate: 3,000 rpm, rotation radius: 2.25 mm), which was placed in an oven having a controlled temperature of 37° C., and then each stirred at 3,000 rpm for 0.5 h, 1 h, 2 h, 4 h, 8 h or 16 h to carry out reaction. In this process, a centrifugal acceleration of about 22.6×g was applied to each analysis chip. For each of the analysis chips, the signal intensity (fluorescence intensity) of the hybridized labeled-aRNA was measured using a high-resolution fluorescence detector. The results thereof are shown in FIGS. 9 and 10 and Table 1. A signal having an intensity of the threshold value or higher was detected 0.5 h after the start of the reaction. Therefore, it was shown that the reaction proceeded rapidly.

Example 4

The test substance solution was injected to the analysis chip 1s (6 sets) in the same manner as in Example 1. The resulting analysis chips were set on a stirring apparatus "MS3 digital", which was placed in an oven having a controlled temperature of 37° C., and then each stirred at 1,000 rpm for 0.5 h, 1 h, 2 h, 4 h, 8 h or 16 h to carry out reaction. In this process, a centrifugal acceleration of about 2.52×g was applied to each analysis chip. For each of the analysis chips, the signal intensity (fluorescence intensity) of the hybridized labeled-aRNA was measured using a high-resolution fluorescence detector. The results thereof are shown in FIGS. 9 and 10 and Table 1. A signal having an intensity of the threshold value or higher was detected 0.5 h after the start of the reaction. Therefore, it was shown that the reaction proceeded rapidly.

Comparative Example 1

The test substance solution was injected to the analysis chip 1s (6 sets) in the same manner as in Example 1. The resulting analysis chips were set on a stirring apparatus "BioShake 5000", which was placed in an oven having a controlled temperature of 37° C., and then each stirred at 1,000 rpm for 0.5 h, 1 h, 2 h, 4 h, 8 h or 16 h to carry out reaction. In this process, a centrifugal acceleration of about 0.671×g was applied to each analysis chip. For each of the analysis chips, the signal intensity (fluorescence intensity) of the hybridized labeled-aRNA was measured using a high-resolution fluorescence detector. The results thereof are shown in FIGS. 9 and 10 and Table 1. At 0.5 h after the start of the reaction, no signal having an intensity of the threshold value or higher was detected. A signal having an intensity of the threshold value or higher was detected after 1 h had passed since the start of the reaction.

Comparative Example 2

The test substance solution was injected to the analysis chip 1s (6 sets) in the same manner as in Example 1. The resulting analysis chips were set on a stirring apparatus "BioShake 5000", which was placed in an oven having a controlled temperature of 37° C., and then each stirred at 250 rpm for 0.5 h, 1 h, 2 h, 4 h, 8 h or 16 h to carry out reaction. In this process, a centrifugal acceleration of about 0.042×g was applied to each analysis chip. For each of the analysis chips, the signal intensity (fluorescence intensity) of the hybridized labeled-aRNA was measured using a high-resolution fluorescence detector. The results thereof are shown in FIGS. 9 and 10 and Table 1. At 0.5 h after the start of the reaction, no signal having an intensity of the threshold value or higher was detected. A signal having an intensity of the threshold value or higher was detected after 1 h had passed since the start of the reaction.

Comparative Example 3

The test substance solution was injected to the analysis chip is (6 sets) in the same manner as in Example 1. The resulting analysis chips were set on a stirring apparatus "MS3 digital", which was placed in an oven having a controlled temperature of 37° C., and then each stirred at 250 rpm for 0.5 h, 1 h, 2 h, 4 h, 8 h or 16 h to carry out reaction. In this process, a centrifugal acceleration of about 0.157×g was applied to each analysis chip. For each of the analysis chips, the signal intensity (fluorescence intensity) of the hybridized labeled-aRNA was measured using a high-resolution fluorescence detector. The results thereof are shown in FIGS. 9 and 10 and Table 1. At 0.5 h after the start of the reaction, no signal having an intensity of the threshold value or higher was detected. A signal having an intensity of the threshold value or higher was detected after 1 h had passed since the start of the reaction.

TABLE 1

Reaction Time and Signal Intensity

| Reaction time (h) | 0.5 | 1 | 2 | 4 | 8 | 16 |
|---|---|---|---|---|---|---|
| Example 1 | 52.5 | 97.8 | 182.5 | 232.3 | 285.5 | 309.0 |
| Example 2 | 41.3 | 85.5 | 171.3 | 218.3 | 279.2 | 305.4 |
| Example 3 | 61.7 | 101.9 | 192.1 | 247.9 | 296.4 | 312.3 |
| Example 4 | 35.3 | 67.5 | 150.9 | 193.5 | 265.4 | 296.4 |
| Comparative Example 1 | 22.8 | 35.3 | 71.2 | 136.7 | 207.2 | 286.4 |
| Comparative Example 2 | 17.8 | 31.2 | 62.9 | 108.3 | 176.1 | 279.0 |
| Comparative Example 3 | 20.5 | 33.9 | 76.8 | 145.4 | 218.9 | 272.9 |

Example 5

To a solution containing 60 ng of the Cy5-labeled aRNA described in Reference Example 1, the hybridization solution was admixed to a volume of 10 μL, and 6.7 μL of the resulting solution was injected to the analysis chip 2s (2 sets). The amount of the injected Cy5-labeled aRNA was 40 ng, which was the same as in Examples 1 to 4. The space of the recess that was not filled with the test substance solution had a volume of about 6.3 μL and the ratio of the space not filled with the test substance solution with respect to the entire recess was about 48%. In the same manner as in Example 1, the analysis chips were set on a stirring apparatus "BioShake 5000" and stirred at 5,000 rpm for 1 hour to carry out reaction. For each of the analysis chips, the signal intensities (fluorescence intensities) of the labeled-aRNA that hybridized to the three genes of b to d were measured using a high-resolution fluorescence detector. The results thereof are shown in Table 2. After 1 hour of reaction time, the signals of all genes had an intensity of the threshold value or higher and were thus effective.

Example 6

To a solution containing 60 ng of the Cy5-labeled aRNA described in Reference Example 1, the hybridization solution was admixed to a volume of 15 μL, and 10 μL of the resulting solution was injected to the analysis chip 2s (2 sets). The amount of the injected Cy5-labeled aRNA was 40 ng, which was the same as in Examples 1 to 4. The space of the recess that was not filled with the test substance solution had a volume of about 6.3 μL and the ratio of the space not filled with the test substance solution with respect to the entire recess was about 23%. In the same manner as in Example 1, the analysis chips were set on a stirring apparatus "BioShake 5000" and stirred at 5,000 rpm for 1 hour to carry out reaction. For each of the analysis chips, the signal intensities (fluorescence intensities) of the labeled-aRNA that hybridized to the three genes of b to d were measured using a high-resolution fluorescence detector. The results thereof are shown in Table 2. After 1 hour of reaction time, the signals of all genes had an intensity of the threshold value or higher and were thus effective.

Comparative Example 4

To a solution containing 60 ng of the Cy5-labeled aRNA described in Reference Example 1, the hybridization solution was admixed to a volume of 20 μL, and 13 μL of the resulting solution was injected to the analysis chip 2s (2 sets) to fill the recess of each analysis chip (the ratio of the space not filled with the test substance solution with respect to the entire recess was 0%). In the same manner as in Example 1, the analysis chips were set on a stirring apparatus "BioShake 5000" and stirred at 5,000 rpm for 1 hour to carry out reaction. For each of the analysis chips, the signal intensities of the labeled-aRNA that hybridized to the three genes of b to d were measured using a high-resolution fluorescence detector. The results thereof are shown in Table 2. After 1 hour of reaction time, the signal of the gene b had an intensity of the threshold value or higher and was thus effective; however, the signal intensity was weaker than the ones measured in Examples 5 and 6. In addition, the signal intensities of the genes c and d were lower than the threshold value and thus invalid.

TABLE 2

Ratio of space not filled with test substance solution in recess and signal intensity of each gene

| | Example 5 | Example 6 | Comparative Example 4 |
|---|---|---|---|
| Ratio of space not filled with test substance solution in recess | 48 | 23 | 0 |
| Gene b | 430.3 | 361.0 | 151.6 |
| | 432.2 | 343.9 | 155.4 |
| Gene c | 139.3 | 129.2 | 107.6 |
| | 147.3 | 132.5 | 107.6 |
| Gene d | 148.7 | 126.3 | 99.9 |
| | 150.6 | 136.5 | 101.7 |
| Threshold value (average + 2SD) | 111.0 | 107.7 | 108.8 |

Reference Example 2

(1) Preparation of Substrate of Analysis Chip

Using the same material as the one used in Reference Example 1, a substrate having external dimensions of 76 mm in length, 26 mm in width and 2.5 mm in thickness was prepared by injection molding. On this substrate, four elliptical recesses having a longer side of 4.8 mm, a shorter side of 2.40 mm and a depth of 1.5 mm were formed and, in each of the recesses, 98 protrusions of 0.1 mm in diameter and 0.12 mm in height were formed (hereinafter, this substrate is referred to as "substrate B"). On this substrate B, the volume of the recesses was about 13.5 μL. The difference in height between the upper surfaces of the protrusions and the upper surface of the flat part and the variation in the height of the upper surfaces of the protrusions were both 3 μm or less. Further, the protrusions were formed at a pitch of 0.18 mm.

(2) Immobilization of Selective Binding Substance (Capturing Probe)

By the same preparation method as in Reference Example 1, as a selective binding substance (capturing probe), an oligonucleotide modified with an amino group at the 5'-end, which was described in an article reporting the research on the differentiation of the types of human papillomavirus (J. Clin. Microbiol., 1995. p. 901-905) and had the base sequence shown in SEQ ID NO:5 (a sequence complementary to a part of the sequence of the L1 gene region of type 16 human papillomavirus, which was used as a test substance), was synthesized. The thus obtained oligonucleotide was spotted and immobilized on 22 of the 98 protrusions of the substrate B to obtain an analysis chip (hereinafter, referred to as "analysis chip 3").

(3) Preparation of Test Substance

As a test substance, a recombinant plasmid purchased from Health Science Research Resources Bank (pHPV16 (full length: 16,600 base pairs), in which genomic DNA of human papillomavirus was cloned, was subjected to ultrasonic fragmentation. The resultant was diluted with 1× hybridization solution (1-wt % bovine serum albumin (BSA), 5×SSC, 1-wt % sodium dodecyl sulfate (SDS), 50 ng/mL salmon sperm DNA solution, 5-wt % dextran sulfate sodium and 30% formamide) to a nucleic acid concentration of 0.1 amol/μL, thereby preparing a sample DNA solution.

(4) Preparation of Detection Probe Solutions

As detection probes to be used in sandwich hybridization, MY11 (SEQ ID NO: 6; based on the base position of the 5'-end when the test substance bound with the capturing probe, a sequence complementary to the 50th to the 69th bases on the 5'-end side), GP5 (SEQ ID NO:7; similarly to MY11, a sequence complementary to the 10th to the 34th bases on the 5'-end side), GP6 (SEQ ID NO:8; based on the base position of the 3'-end when the test substance bound with the capturing probe, a sequence complementary to the 60th to the 82nd bases on the 3'-end side) and MY09 (SEQ ID NO:9; similarly to GP6, a sequence complementary to the 340th to the 359th bases on the 3'-end side), all of which were labeled with biotin at both the 3'-end and the 5'-end, were synthesized. These detection probes were each diluted with sterilized water to a concentration of 100 fmol to prepare detection probe solutions.

Example 7

To 1 μL of the sample DNA solution described in Reference Example 2, 1 μL of each of the detection probe solutions described in Reference Example 2 was added and mixed, and the resulting mixture was heated in a thermal cycler at 95° C. for 5 minutes. After leaving the mixture to stand until it was cooled to room temperature, 8 μL of 1× hybridization solution described in Reference Example 2 was added thereto and mixed, thereby preparing each test substance-containing hybridization solution. The entire amount of the respective test substance-containing hybridization solutions was injected into one of the recesses of the analysis chip 3 and the opening was sealed with a PET film coated with an acrylic adhesive. The space of the recess that was not filled with the solution had a volume of about 3.5 μL and the ratio of the space not filled with the solution in the recess was about 26%. By a sandwich hybridization method, detection of the test substance was carried out. The analysis chips were set on a stirring apparatus "BioShake 5000" (manufactured by Q. Instruments GmbH), which was placed in an oven having a controlled temperature of 32° C., and stirred at 3,000 rpm for 2 hours to allow the capturing probe and the test substance to undergo hybridization reaction. In this process, a centrifugal acceleration of about 6.04×g was applied to each analysis chip. After the reaction, the seal covering the opening was removed and the analysis chips were washed for 5 minutes with a washing solution A heated to 30° C. (0.5×SSC and 1-wt % SDS). After drying the analysis chips, 10 μL of 50 ng/μL streptavidin phycoerythrin solution, which was prepared by mixing a staining reagent (streptavidin phycoerythrin) and a diluent (100 mM MES, 1M NaCl, 0.05-wt % Tween 20 and 2 mg/mL BSA), was added dropwise to the recess, and the analysis chips were incubated in the dark at 35° C. for 5 minutes. Thereafter, the analysis chips were washed for 5 minutes with a washing solution B heated to 30° C. (6×SSPE and 0.01-wt % Tween 20) and then dried. The signal intensity (fluorescence intensity) was measured using a high-resolution fluorescence detector ("3D-Gene (registered trademark) Scanner", manufactured by Toray Industries, Inc.). The values were read for the protrusions on which the selective binding substance was immobilized (signal) and for the protrusions on which the selective binding substance was not immobilized (noise) so as to calculate the signal/noise ratio (S/N ratio). The results thereof are shown in Table 3. The S/N ratio was 2.80, which was higher than the detection limit of S/N=2.

Example 8

The same operations as in Example 7 were carried out, except that the rotation rate of the stirring apparatus at the time of performing the hybridization reaction was changed to 5,000 rpm. In this case, the centrifugal acceleration was 16.77×g. The result of calculating the S/N ratio is shown in Table 3. The S/N ratio was 2.53, which was higher than the detection limit of S/N=2.

Comparative Example 5

The same operations as in Example 7 were carried out, except that the rotation rate of the stirring apparatus at the time of performing the hybridization reaction was changed to 1,000 rpm. In this case, the centrifugal acceleration was 0.67×g. The result of calculating the S/N ratio is shown in Table 3. The S/N ratio was 1.56, which was lower than the detection limit of S/N=2.

Example 9

The same operations as in Example 7 were carried out, except that "Mix-EVR" (manufactured by Taitec Corporation; maximum rotation rate: 2,500 rpm, rotation radius: 1 mm) was used as the stirring apparatus and the rotation rate thereof at the time of performing the hybridization reaction was set at 2,000 rpm. In this case, the centrifugal acceleration was 4.47×g. The result of calculating the S/N ratio is shown in Table 3. The S/N ratio was 2.24, which was higher than the detection limit of S/N=2.

Example 10

The same operations as in Example 9 were carried out, except that the rotation rate of the stirring apparatus at the time of performing the hybridization reaction was changed to 2,500 rpm. In this case, the centrifugal acceleration was 6.99×g. The result of calculating the S/N ratio is shown in Table 3. The S/N ratio was 2.76, which was higher than the detection limit of S/N=2.

Comparative Example 6

The same operations as in Example 9 were carried out, except that the rotation rate of the stirring apparatus at the time of performing the hybridization reaction was changed to 500 rpm. In this case, the centrifugal acceleration was 0.28×g. The result of calculating the S/N ratio is shown in Table 3. The S/N ratio was 1.48, which was lower than the detection limit of S/N=2.

Example 11

The same operations as in Example 7 were carried out, except that "MS3 digital" (manufactured by IKA) was used as the stirring apparatus and the rotation rate thereof at the time of performing the hybridization reaction was set at 2,000 rpm. In this case, the centrifugal acceleration was 10.06×g. The result of calculating the S/N ratio is shown in Table 3. The S/N ratio was 3.25, which was higher than the detection limit of S/N=2.

Example 12

The same operations as in Example 10 were carried out, except that the rotation rate of the stirring apparatus at the time of performing the hybridization reaction was changed to 3,000 rpm. In this case, the centrifugal acceleration was 22.64×g. The result of calculating the S/N ratio is shown in Table 3. The S/N ratio was 2.72, which was higher than the detection limit of S/N=2.

Comparative Example 7

The same operations as in Example 11 were carried out, except that the rotation rate of the stirring apparatus at the time of performing the hybridization reaction was changed to 500 rpm. In this case, the centrifugal acceleration was 0.63×g. The result of calculating the S/N ratio is shown in Table 3. The S/N ratio was 1.61, which was lower than the detection limit of S/N=2.

Example 13

The same operations as in Example 7 were carried out, except that a manufactured stirring apparatus (maximum rotation rate: 1,000 rpm, rotation radius: 5 mm) was used and the rotation rate thereof at the time of performing the hybridization reaction was set at 1,000 rpm. In this case, the centrifugal acceleration was 5.59×g. The result of calculating the S/N ratio is shown in Table 3. The S/N ratio was 2.39, which was higher than the detection limit of S/N=2.

Comparative Example 8

The same operations as in Example 13 were carried out, except that the rotation rate of the stirring apparatus at the time of performing the hybridization reaction was changed to 250 rpm. In this case, the centrifugal acceleration was 0.35×g. The result of calculating the S/N ratio is shown in Table 3. The S/N ratio was 1.49, which was lower than the detection limit of S/N=2.

Comparative Example 9

The same operations as in Example 7 were carried out, except that "Multi Shaker MMS-210" (manufactured by Tokyo Rikakikai Co., Ltd.; maximum rotation rate: 250 rpm, rotation radius: 12.5 mm) was used as the stirring apparatus and the rotation rate thereof at the time of performing the hybridization reaction was set at 250 rpm. In this case, the centrifugal acceleration was 0.87×g. The result of calculating the S/N ratio is shown in Table 3. The S/N ratio was 1.56, which was lower than the detection limit of S/N=2.

Comparative Example 10

The same operations as in Example 7 were carried out, except that a manufactured stirring apparatus (maximum rotation rate: 1,000 rpm, rotation radius: 24 mm) was used and the rotation rate thereof at the time of performing the hybridization reaction was set at 100 rpm. In this case, the centrifugal acceleration was 0.27×g. The result of calculating the S/N ratio is shown in Table 3. The S/N ratio was 1.39, which was lower than the detection limit of S/N=2.

Comparative Example 11

The same operations as in Example 7 were carried out, except that a manufactured stirring apparatus (maximum rotation rate: 1,000 rpm, rotation radius: 72 mm) was used and the rotation rate thereof at the time of performing the hybridization reaction was set at 100 rpm. In this case, the centrifugal acceleration was 0.80×g. The result of calculating the S/N ratio is shown in Table 3. The S/N ratio was 1.57, which was lower than the detection limit of S/N=2.

TABLE 3

Rotation radius, rotation rate, centrifugal acceleration and signal intensity

| | Rotation radius (mm) | Rotation rate (rpm) | Centrifugal acceleration (×g) | Signal intensity | | |
|---|---|---|---|---|---|---|
| | | | | Signal | Noise | S/N ratio |
| Comparative Example 5 | 0.6 | 1,000 | 0.67 | 2,841 | 1,821 | 1.56 |
| Example 7 | 0.6 | 3,000 | 6.04 | 5,110 | 1,825 | 2.80 |
| Example 8 | 0.6 | 5,000 | 16.77 | 4,625 | 1,828 | 2.53 |
| Comparative Example 6 | 1 | 500 | 0.28 | 2,700 | 1,824 | 1.48 |
| Example 9 | 1 | 2,000 | 4.47 | 4,036 | 1,802 | 2.24 |
| Example 10 | 1 | 2,500 | 6.99 | 5,029 | 1,822 | 2.76 |
| Comparative Example 7 | 2.25 | 500 | 0.63 | 2,924 | 1,816 | 1.61 |
| Example 11 | 2.25 | 2,000 | 10.06 | 5,879 | 1,809 | 3.25 |
| Example 12 | 2.25 | 3,000 | 22.64 | 4,967 | 1,826 | 2.72 |
| Comparative Example 8 | 5 | 250 | 0.35 | 2,713 | 1,821 | 1.49 |
| Example 13 | 5 | 1,000 | 5.59 | 4,338 | 1,815 | 2.39 |
| Comparative Example 9 | 12.5 | 250 | 0.87 | 2,838 | 1,819 | 1.56 |
| Comparative Example 10 | 24 | 100 | 0.27 | 2,538 | 1,826 | 1.39 |
| Comparative Example 11 | 72 | 100 | 0.80 | 2,820 | 1,796 | 1.57 |

Example 14

To 4 μL of the sample DNA solution described in Reference Example 2, 4 μL of each of the detection probe solutions described in Reference Example 2 was added and mixed, and the resulting mixture was heated in a thermal cycler at 95° C. for 5 minutes. After leaving the mixture to stand until it was cooled to room temperature, 32 μL of 1×hybridization solution described in Reference Example 2 was added thereto and mixed, thereby preparing each test substance-containing hybridization solution. To each of four recesses (recess Nos. 1 to 4) of the analysis chip 3, 10 μL of each test substance-containing solution was injected and the openings were sealed with a PET film coated with an acrylic adhesive. The space of each recess that was not filled with the solution had a volume of about 3.5 μL and the ratio of the space not filled with the solution in each recess was about 26%. By a sandwich hybridization method, detection of the test substance was carried out. The analysis chip was set on a stirring apparatus "MS3 digital" (manufactured by IKA), which was placed in an oven having a controlled temperature of 32° C., and stirred at 2,000 rpm for 2 hours to allow the capturing probe and the test substance to undergo hybridization reaction. In this process, a centrifugal acceleration of about 10.1×g was applied to the analysis chip. After the reaction, the seal covering the openings was removed and the analysis chips were washed for 5 minutes with the washing solution A heated to 30° C. (0.5×SSC and 1-wt % SDS). After drying the analysis chip, 10 μL of 50 ng/μL streptavidin phycoerythrin solution, which was prepared by mixing a staining reagent (streptavidin phycoerythrin) and a diluent (100 mM MES, 1M NaCl, 0.05-wt % Tween 20 and 2 mg/mL BSA), was added dropwise to each recess, and the analysis chip was incubated in the dark at 35° C. for 5 minutes. Thereafter, the analysis chip was washed for 5 minutes with the washing solution B heated to 30° C. (6×SSPE and 0.01-wt % Tween 20) and then dried. The signal intensity (fluorescence intensity) was measured using a high-resolution fluorescence detector ("3D-Gene (registered trademark) Scanner", manufactured by Toray Industries, Inc.). The values were read for the protrusions on which the selective binding substance was immobilized (signal) and for the protrusions on which the selective binding substance was not immobilized (noise) so as to calculate the signal/noise ratio (S/N ratio) for each of the four recesses (recess Nos. 1 to 4). The results thereof are shown in Table 4. The S/N ratio was found to be 2.9, 2.7, 2.8 and 2.8 for the recess Nos. 1 to 4, respectively, all of which values were higher than the detection limit of S/N=2. In addition, the CV values of the signals of the 22 protruded spots in the respective recesses were all less than 10%, and the signal variation within each recess was small. Moreover, the CV value of the signals of all of the four recesses (88 signals) was also small at 7.5%. Therefore, it was shown that variation among the recesses was also small.

Comparative Example 12

The same operations as in Example 14 were carried out, except that a manufactured rotary revolution-type stirring apparatus (revolution radius: 72 mm) was used and the revolution rate was set at 350 rpm. In this case, the centrifugal acceleration was 9.9×g. The results of calculating the S/N ratio for the four recesses (recess Nos. 1 to 4) are shown in Table 4. The S/N ratio was 1.8, 1.9, 1.7 and 1.5 for the four recesses, respectively, all of which values were lower than the detection limit of S/N=2. In addition, the CV values of the signals of the 22 protruded spots in the respective recesses were variable around 10% and the CV value of the signals of all of the four recesses (88 signals) was high at 15.3%. Therefore it was shown that variation among the recesses was large.

TABLE 4

Rotation mode of stirring, signal intensity, variation and S/N ratio

|  |  | Example 14 | | | | Comparative Example 12 | | | |
| --- | --- | --- | --- | --- | --- | --- | --- | --- | --- |
| Rotation mode | | rotation | | | | rotation and revolution | | | |
| Rotation radius | | 2.25 mm | | | | 72 mm | | | |
| Rotation rate | | 2,000 rpm | | | | 350 rpm | | | |
| Centrifugal acceleration | | 10.1 × g | | | | 9.9 × g | | | |

|  |  | Recess No. | | | | | | | |
| --- | --- | --- | --- | --- | --- | --- | --- | --- | --- |
|  |  | #1 | #2 | #3 | #4 | #1 | #2 | #3 | #4 |
| Signal of each recess | Average | 5,395 | 5,273 | 5,262 | 5,132 | 3,322 | 3,566 | 3,018 | 2,747 |
|  | Standard deviation | 453 | 339 | 452 | 302 | 299 | 283 | 297 | 476 |
|  | CV (%) | 8.4 | 6.4 | 8.6 | 5.9 | 9.0 | 7.9 | 9.9 | 10.8 |
| Overall signal | Average | 5,266 | | | | 3,112 | | | |
|  | Standard deviation | 396.6 | | | | 475.6 | | | |
|  | CV (%) | 7.5 | | | | 15.3 | | | |
| Noise average of each recess | | 1,874 | 1,938 | 1,859 | 1,862 | 1,820 | 1,847 | 1,757 | 1,777 |
| S/N ratio | | 2.9 | 2.7 | 2.8 | 2.8 | 1.8 | 1.9 | 1.7 | 1.5 |

INDUSTRIAL APPLICABILITY

The method of stirring a solution is capable of, as compared to before, largely shortening the time required for detection or quantification of a test substance using an analysis chip such as a DNA chip. Therefore, the present invention is useful since it enables prompt diagnosis, examination and the like of diseases in clinical practice as well as at examination centers.

The invention claimed is:

1. A method of stirring a test substance-containing solution injected into an analysis chip, wherein said analysis chip comprises a recess to which said test substance-containing solution is injected; and a selective binding substance, which selectively binds to said test substance, is immobilized on the entirety or a part of the bottom surface of said recess, said method comprising:
   injecting said test substance-containing solution to the space in said recess of said analysis chip such that said space is partially left unfilled; and
   rotating said analysis chip to which said test substance-containing solution is injected at a rotation radius of 0.1 mm to 10 mm to apply a centrifugal acceleration of not less than 1×g.

2. The method according to claim 1, wherein said test substance-containing solution is injected into said recess such that 10% to 70% of said space is left unfilled.

3. The method according to claim 1, wherein said analysis chip comprises plural recesses to which said test substance-containing solution is injected, said plural recesses being separated by a wall(s) from one another.

4. The method according to claim 1, wherein said analysis chip is fitted with a cover that covers the entirety of said recess(es); and said test substance-containing solution is sealed in said recess(es).

5. The method according to claim 1, wherein said analysis chip to which said test substance-containing solution is injected is arranged such that the bottom surface(s) of said recess(es) is/are horizontal or tilted at 0° to 3° with respect to a horizontal plane; and said analysis chip is rotated in a horizontal or tilted direction.

6. A method of analyzing a test substance comprising:
   allowing said test substance to bind to a selective binding substance immobilized on an analysis chip by the method of stirring a solution according to claim 1; and
   detecting said test substance bound to said selective binding substance.

7. The method according to claim 2, wherein said analysis chip comprises plural recesses to which said test substance-containing solution is injected, said plural recesses being separated by a wall(s) from one another.

8. The method according to claim 2, wherein said analysis chip is fitted with a cover that covers the entirety of said recess(es); and said test substance-containing solution is sealed in said recess(es).

9. The method according to claim 3, wherein said analysis chip is fitted with a cover that covers the entirety of said recess(es); and said test substance-containing solution is sealed in said recess(es).

10. The method according to claim 2, wherein said analysis chip to which said test substance-containing solution is injected is arranged such that the bottom surface(s) of said recess(es) is/are horizontal or tilted at 0° to 3° with respect to a horizontal plane; and said analysis chip is rotated in a horizontal or tilted direction.

11. The method according to claim 3, wherein said analysis chip to which said test substance-containing solution is injected is arranged such that the bottom surface(s) of said recess(es) is/are horizontal or tilted at 0° to 3° with respect to a horizontal plane; and said analysis chip is rotated in a horizontal or tilted direction.

12. The method according to claim 4, wherein said analysis chip to which said test substance-containing solution is injected is arranged such that the bottom surface(s) of said recess(es) is/are horizontal or tilted at 0° to 3° with respect to a horizontal plane; and said analysis chip is rotated in a horizontal or tilted direction.

* * * * *